US010182765B2

(12) United States Patent
Fishler et al.

(10) Patent No.: US 10,182,765 B2
(45) Date of Patent: Jan. 22, 2019

(54) SYSTEMS AND METHODS FOR CLASSIFYING SIGNALS OF INTEREST IN A CARDIAC RHYTHM MANAGEMENT DEVICE

(71) Applicant: Pacesetter, Inc., Sunnyvale, CA (US)

(72) Inventors: Matthew G. Fishler, Santa Cruz, CA (US); Gene A. Bornzin, Simi Valley, CA (US); Benjamin T. Persson, Sunnyvale, CA (US); Kenneth J. Carroll, Los Altos, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 574 days.

(21) Appl. No.: 14/862,810

(22) Filed: Sep. 23, 2015

(65) Prior Publication Data
US 2017/0079595 A1    Mar. 23, 2017

(51) Int. Cl.
 *A61B 5/04*  (2006.01)
 *A61B 5/00*  (2006.01)
 *A61N 1/365* (2006.01)

(52) U.S. Cl.
 CPC ........ *A61B 5/7264* (2013.01); *A61B 5/04014* (2013.01); *A61N 1/36507* (2013.01)

(58) Field of Classification Search
 CPC .............. A61B 5/7264; A61B 5/04014; A61N 1/36507
 See application file for complete search history.

(56) References Cited

U.S. PATENT DOCUMENTS

2008/0109041 A1 *  5/2008  de Voir .............. A61B 5/04017
                                                              607/7

* cited by examiner

*Primary Examiner* — Lindsey G Wehrheim

(57) ABSTRACT

The present disclosure provides systems and methods for classifying signals of interest in a cardiac rhythm management (CRM) device. A CRM device includes an intrinsic activation sensing circuit configured to pass signals falling within a first passband, a crosstalk sensing circuit configured to pass signals falling within a second passband, wherein the second passband contains higher frequencies than the first passband, and a computing device communicatively coupled to the intrinsic activation sensing circuit and the crosstalk sensing circuit, the computing device configured to classify a signal of interest as one of an intrinsic activation signal and a crosstalk signal based on whether the signal of interest is passed by the intrinsic activation sensing circuit and the crosstalk sensing circuit.

20 Claims, 8 Drawing Sheets

SYSTEMS AND METHODS FOR CLASSIFYING SIGNALS OF INTEREST IN A CARDIAC RHYTHM MANAGEMENT DEVICE

FIELD OF THE DISCLOSURE

The present disclosure relates generally to cardiac rhythm management devices, and more particularly to discriminating between intrinsic activation signals and crosstalk signals in cardiac rhythm management devices.

BACKGROUND ART

Multi-chamber cardiac rhythm management (CRM) devices include, for example, dual-chamber pacemakers and implantable defibrillators. In such devices, there is a risk that a pacing pulse (or similar pulse) delivered at one location within a patient's heart (e.g., the right atrium) may be detected by electrodes and associated sense circuitry in another location within the patient's heart (e.g., the right ventricle). This event is referred to as crosstalk.

This crosstalk, if not properly recognized, may be sensed and misclassified as an intrinsic local activation event, such as a premature ventricular contraction (PVC). In the event of such a misclassification, improper actions may be taken (e.g., withholding the next pace pulse as part of a PVC response algorithm). Accordingly, it is desirable to accurately discriminate crosstalk from intrinsic activations.

BRIEF SUMMARY OF THE DISCLOSURE

In one embodiment, the present disclosure is directed to a cardiac rhythm management (CRM) device. The CRM device includes an intrinsic activation sensing circuit configured to pass signals falling within a first passband, a crosstalk sensing circuit configured to pass signals falling within a second passband, wherein the second passband contains higher frequencies than the first passband, and a computing device communicatively coupled to the intrinsic activation sensing circuit and the crosstalk sensing circuit, the computing device configured to classify a signal of interest as one of an intrinsic activation signal and a crosstalk signal based on whether the signal of interest is passed by the intrinsic activation sensing circuit and the crosstalk sensing circuit.

In another embodiment, the present disclosure is directed to a method of classifying a signal of interest using a cardiac rhythm management (CRM) device. The method includes receiving the signal of interest at an intrinsic activation sensing circuit configured to pass signals falling within a first passband, receiving the signal of interest at a crosstalk sensing circuit configured to pass signals falling within a second passband, wherein the second passband contains higher frequencies than the first passband, determining, using a computing device, whether the signal of interest is passed by the intrinsic activation sensing circuit and the crosstalk sensing circuit, and classifying the signal of interest as one of an intrinsic activation signal and a crosstalk signal based on the determination.

In another embodiment, the present disclosure is directed to a computing device for use in classifying a signal of interest detected by a cardiac rhythm management (CRM) device. The computing device includes a memory device, and a processor communicatively coupled to the memory device, the processor configured to determine whether the signal of interest is passed by an intrinsic activation sensing circuit configured to pass signals falling within a first passband, determine whether the signal of interest is passed by a crosstalk sensing circuit configured to pass signals falling within a second passband, wherein the second passband contains higher frequencies than the first passband, and classify the signal of interest as one of an intrinsic activation signal and a crosstalk signal based on whether the signal of interest is passed by the intrinsic activation sensing circuit and the crosstalk sensing circuit.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The present disclosure provides a cardiac rhythm management (CRM) device with a crosstalk sensing circuit in addition to at least one intrinsic activation sensing circuit configured to sense typical intrinsic activity (e.g., P/R waves, evoked responses, etc.). The crosstalk sensing circuit has a passband that is shifted to significantly higher frequencies than the intrinsic activation sensing circuit. This enables the crosstalk sensing circuit to be more discriminative of relatively fast rising and falling edges of a locally-sensed crosstalk signal produced, for example, by a remote pacing pulse. Accordingly, signals detected by both the intrinsic activation sensing circuit and the crosstalk sensing circuit can, with a relatively high degree of confidence, be identified as crosstalk rather than intrinsic activity.

Figure 1:
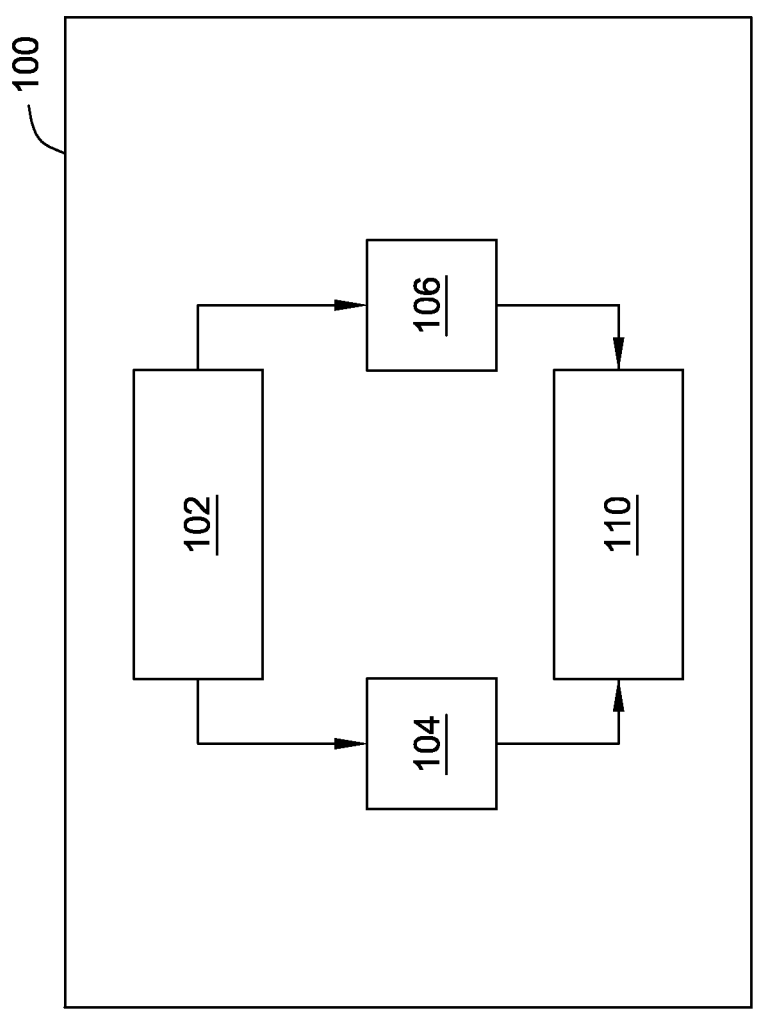
FIG. 1 is a block diagram of one embodiment of a cardiac rhythm management (CRM) device.

With reference to FIG. 1, a cardiac rhythm management (CRM) device is indicated generally at 100. CRM device 100 may be, for example, a dual-chamber pacemaker, an implantable defibrillator, and/or a leadless medical device. Alternatively, CRM device 100 may be any type of assistive cardiac device capable of implementing the methods and systems described herein.

CRM device 100 senses local events via a pair of sensing electrodes 102. The sensed events may be, for example, intrinsic activation events and/or crosstalk events. The sensed signals are then processed by at least one intrinsic activation sensing circuit 104. Intrinsic activation sensing circuit 104 may be, for example, an amplifier that has a predefined passband designed to provide desired signal-tonoise performance that passes relevant signals (e.g., intrinsic activations) while rejecting irrelevant signals (e.g., noise, baseline drift, etc.). An upper tail of the predefined passband may at least partially overlap with frequency content of a crosstalk signal. Accordingly, intrinsic activation sensing circuit 104 may inadvertently pass at least some energy content derived from crosstalk signals.

Figure 2:
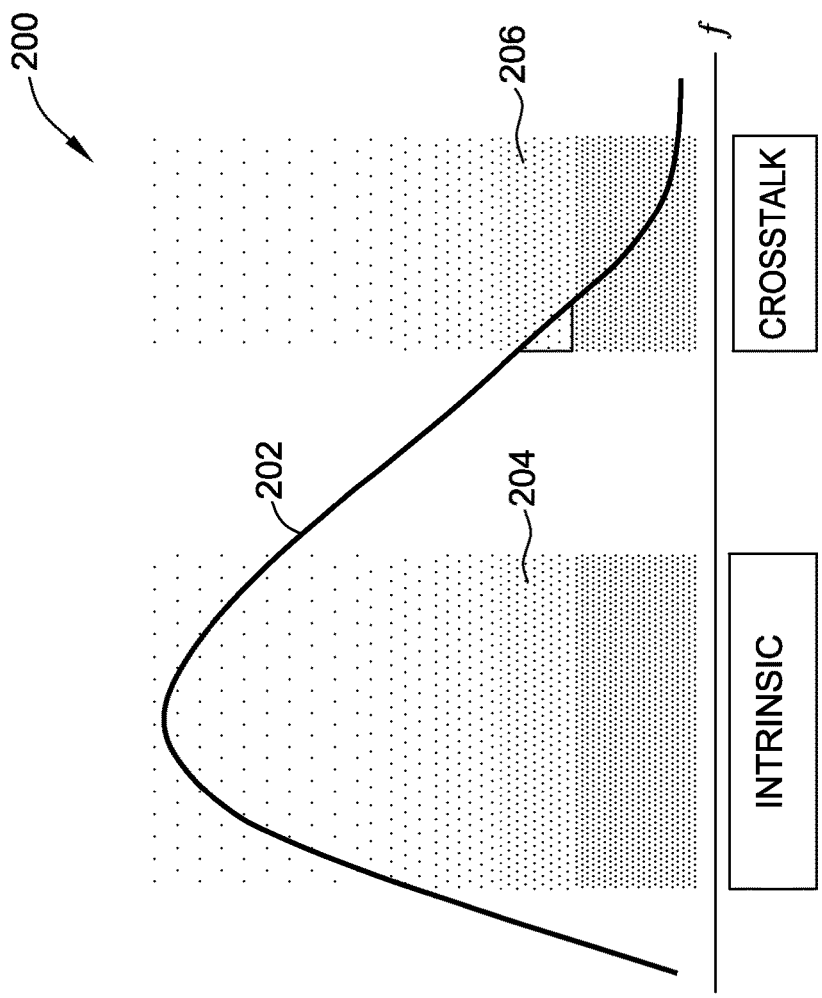
FIG. 2 is a frequency diagram including a passband for one embodiment of an intrinsic activation sensing circuit.

FIG. 2 is a frequency diagram 200 illustrating an example passband 202 for intrinsic activation sensing circuit 104. Diagram 200 also shows an intrinsic activation band 204 and a crosstalk band 206 that represent the bands of potential frequency content of intrinsic activation signals and crosstalk signals, respectively. As shown in FIG. 2, passband 202 passes at least some crosstalk signals falling within crosstalk band 206. The likelihood of detecting (i.e., passing) crosstalk signals is further increased as the sensitivity of intrinsic activation sensing circuit 104 is increased and/or the amplitude of the crosstalk signals are increased.

Accordingly, as shown in FIG. 1, in this embodiment, CRM device 100 includes a crosstalk sensing circuit 106 that has a passband shifted to higher frequencies, as compared to intrinsic activation sensing circuit 104. As described herein, the passband of crosstalk sensing circuit 106 passes frequency content of crosstalk signals with greater sensitivity than intrinsic activation sensing circuit 104. Further, a lower cutoff frequency of the passband of crosstalk sensing circuit 106 is sufficiently greater than the frequency content of intrinsic activation signals such that crosstalk sensing circuit 106 substantially rejects any intrinsic activation signals.

Figure 3:
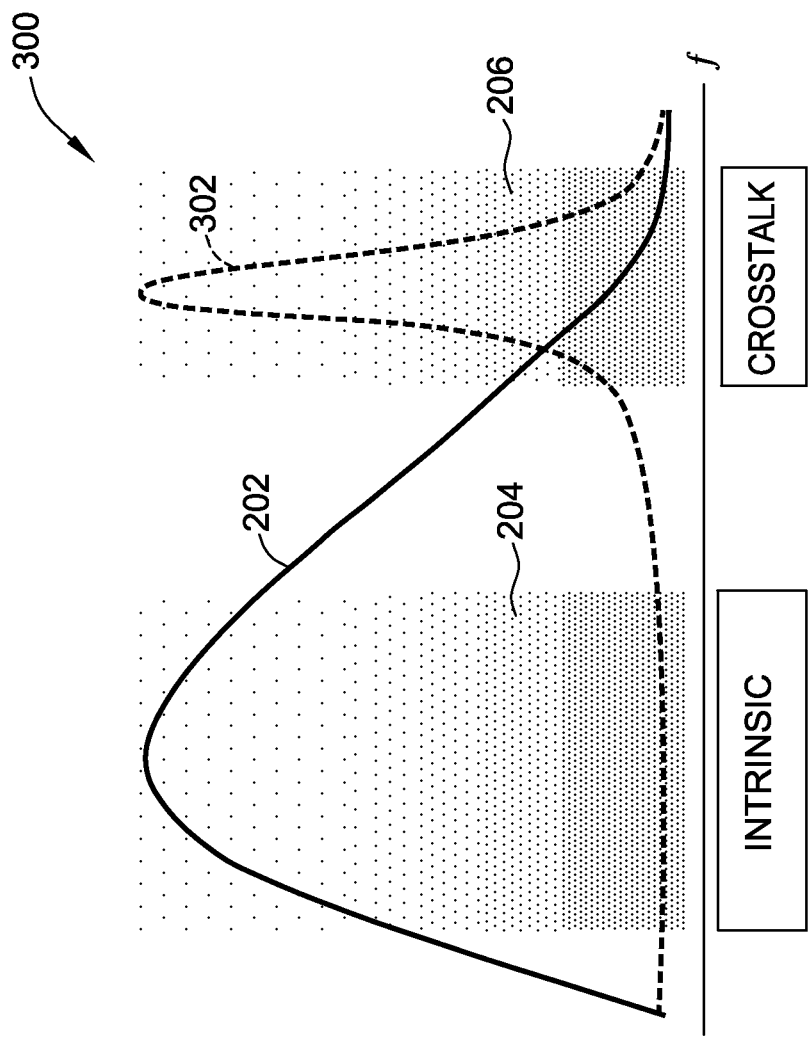
FIG. 3 is a frequency diagram including a passband for one embodiment of a crosstalk sensing circuit.

FIG. 3 is a frequency diagram 300 illustrating an example passband 302 for crosstalk sensing circuit 106, as well as passband 202 for intrinsic activation sensing circuit 104. As shown in FIG. 3, as compared to passband 202, passband 302 is preferentially sensitive to signals in crosstalk band 206. Further, passband 302 is insensitive to signals in intrinsic activation band 204. Accordingly, in operation, passband 302 passes crosstalk signals and rejects intrinsic activation signals.

To accurately discriminate crosstalk due to a remote pacing pulse from local intrinsic activity, CRM device 100 takes advantage of the fact that each pacing pulse has nearly-instantaneous voltage discontinuities at its leading and trailing edges that are associated with the initiation and termination of that pacing pulse. These voltage discontinuities are not present in intrinsic activity events, and accordingly, can be used to discriminate between crosstalk and intrinsic activity. For example, the frequency content of intrinsic activity is almost always less than 300 Hertz (Hz). Therefore, passband 302 is shifted to significantly higher frequencies relative to passband 202. That is, in this embodiment, passband 302 is located at frequencies associated with the fast rising and falling edges of a remote pacing pulse. Further, pacing pulses are generally much shorter than intrinsic activations. That is, pacing pulses may generally be between 0.1 milliseconds (ms) and 1.5 ms (e.g., 0.4-0.5 ms). This relatively short length also contributes to the pacing pulses being located in a higher frequency band.

Passband 302 extends from a lower cutoff frequency to an upper cutoff frequency. The lower cutoff frequency may be, for example, greater than or equal to 500 Hz, greater than or equal to 1000 Hz, greater than or equal to 5000 Hz, etc. The higher the lower cutoff frequency is, the more discriminatory passband 302 is of the voltage discontinuity in crosstalk due to a remote pacing pulse. In some embodiments, passband 302 may have a center frequency of approximately 25,000 Hz. Accordingly, passband 302 has a frequency range significantly higher than that of passband 202.

Referring back to FIG. 1, in this embodiment, CRM device 100 includes a computing device 110 coupled to intrinsic activation sensing circuit 104 and crosstalk sensing circuit 106. Computing device 110 determines, based on an output of intrinsic activation sensing circuit 104 and crosstalk sensing circuit 106, whether a signal of interest is a crosstalk signal or an intrinsic activation signal, as described herein.

Figure 4:
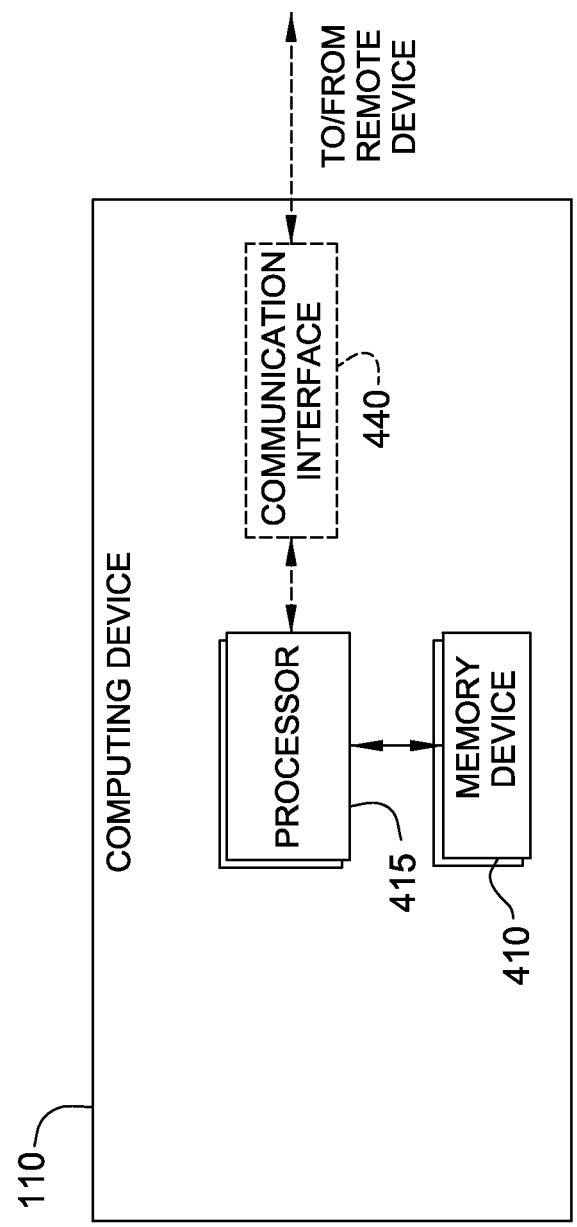
FIG. 4 is a block diagram of one embodiment of a computing device that may be used with the CRM device shown in FIG. 1.

FIG. 4 is a block diagram of one embodiment of computing device 110 that may be used with CRM device 100 (shown in FIG. 1). Computing device 110 includes at least one memory device 410 and a processor 415 that is coupled to memory device 410 for executing instructions. In some embodiments, executable instructions are stored in memory device 410. In the illustrated embodiment, computing device 110, and by extension CRM device 100, performs one or more operations described herein by programming processor 415. For example, processor 415 may be programmed by encoding an operation as one or more executable instructions and by providing the executable instructions in memory device 410.

Processor 415 may include one or more processing units (e.g., in a multi-core configuration). Further, processor 415 may be implemented using one or more heterogeneous processor systems in which a main processor is present with secondary processors on a single chip. In another illustrative example, processor 415 may be a symmetric multi-processor system containing multiple processors of the same type. Further, processor 415 may be implemented using any suitable programmable circuit including one or more systems and microcontrollers, microprocessors, reduced instruction set circuits (RISC), application specific integrated circuits (ASIC), programmable logic circuits, field programmable gate arrays (FPGA), and any other circuit capable of executing the functions described herein. In the illustrated embodiment, processor 415 determines, based on an output of intrinsic activation sensing circuit 104 and crosstalk sensing circuit 106, whether a signal of interest is a crosstalk signal or an intrinsic activation signal, as described herein.

In the illustrated embodiment, memory device 410 is one or more devices that enable information such as executable instructions and/or other data to be stored and retrieved. Memory device 410 may include one or more computer readable media, such as, without limitation, dynamic random access memory (DRAM), read-only memory (ROM), electrically erasable programmable read-only memory (EEPROM), static random access memory (SRAM), a solid state disk, and/or a hard disk. Memory device 410 may be configured to store, without limitation, application source code, application object code, source code portions of interest, object code portions of interest, configuration data, execution events and/or any other type of data.

Computing device 110, in the illustrated embodiment, includes a communication interface 440 coupled to processor 415. Communication interface 440 communicates with one or more remote devices, such as a clinician or patient programmer, or another CRM device. To communicate with remote devices, communication interface 440 may include, for example, a wired network adapter, a wireless network adapter, a radio-frequency (RF) adapter, and/or a mobile telecommunications adapter. For example, programmer to implant ("p2i") and/or implant to implant ("i2i") communication may be used. In some embodiments, an i2i sensing channel is leveraged to implement crosstalk sensing circuit 106.

Figure 5:
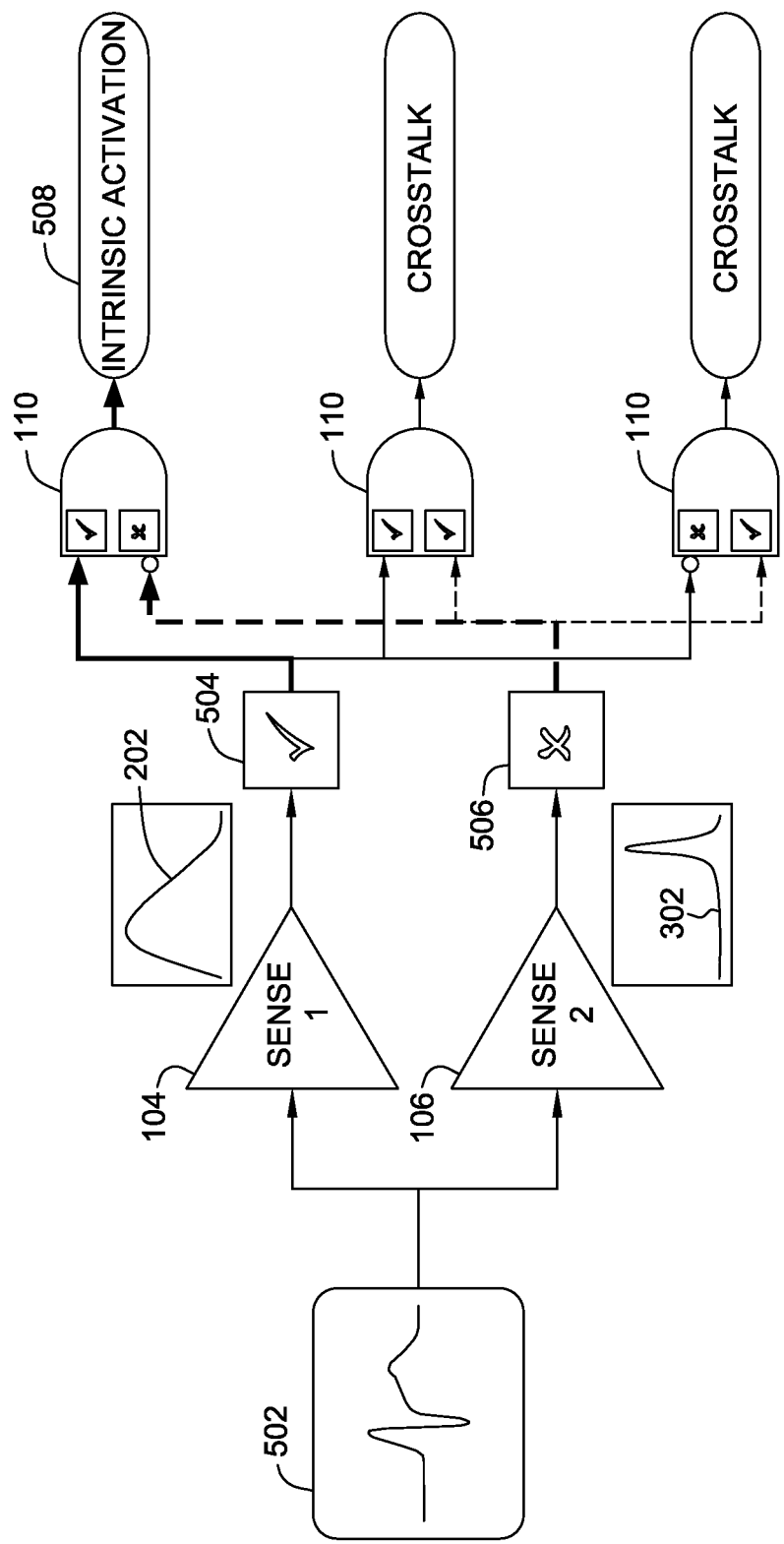
FIG. 5 is a diagram illustrating a response to an intrinsic activation signal by the CRM device shown in FIG. 1.
Figure 6:
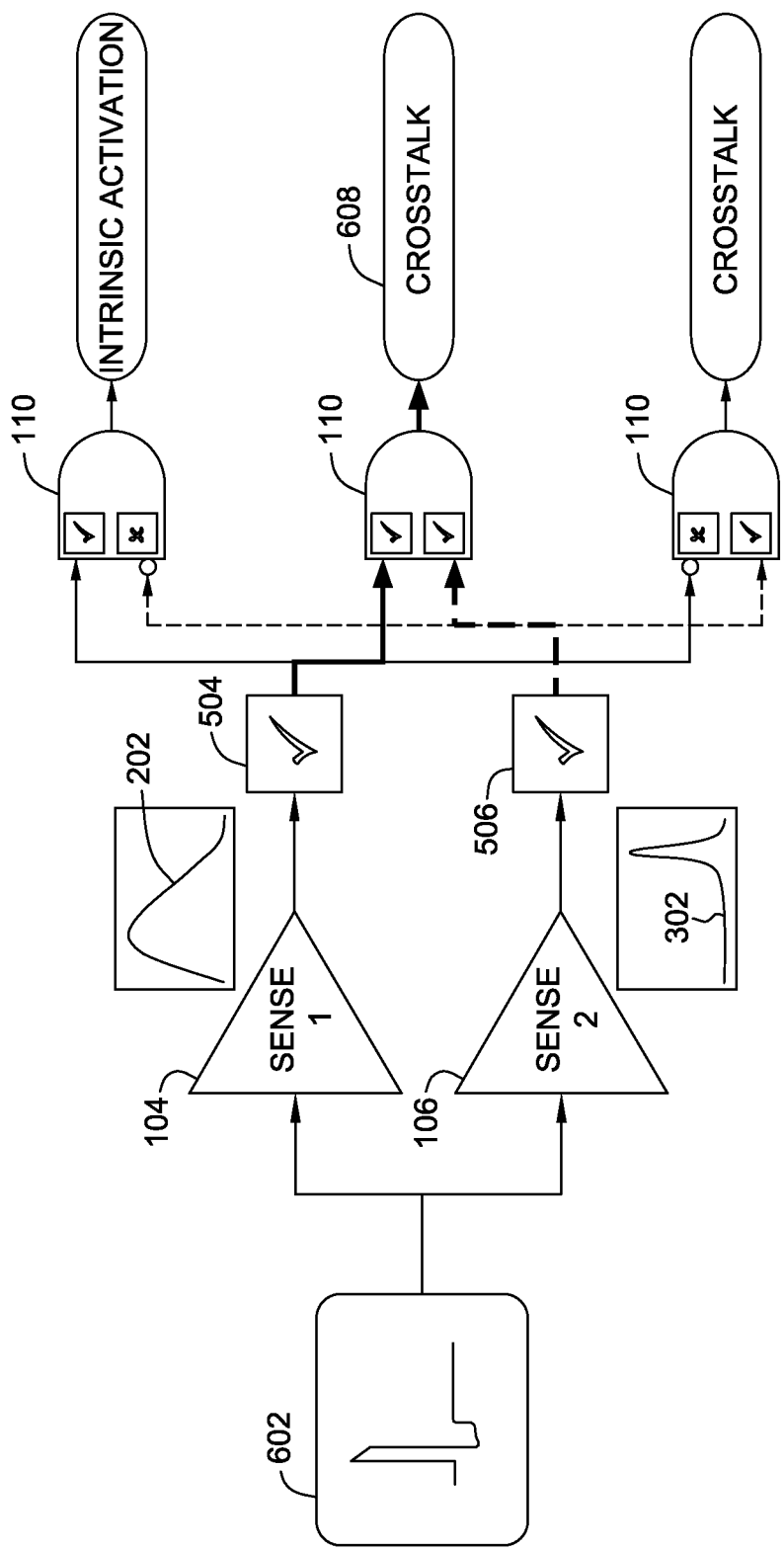
FIG. 6 is a diagram illustrating a response to a crosstalk signal by the CRM device shown in FIG. 1.
Figure 7:
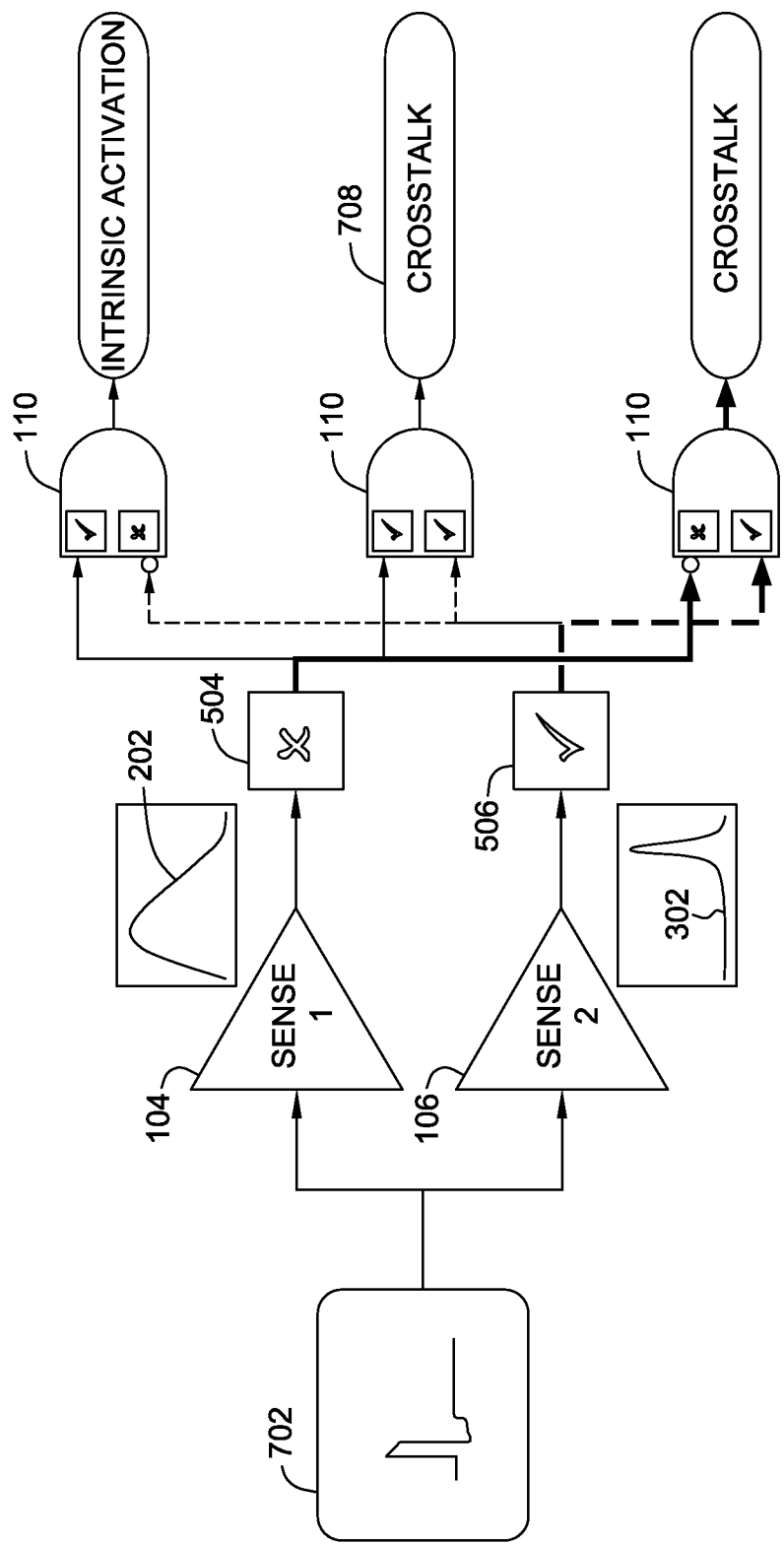
FIG. 7 is a diagram illustrating a response to a crosstalk signal by the CRM device shown in FIG. 1.

FIGS. 5-7 schematically illustrate how CRM device 100 distinguishes between crosstalk signals and intrinsic activation signals using intrinsic activation sensing circuit 104 and crosstalk sensing circuit 106.

FIG. 5 illustrates a response by CRM device 100 to an intrinsic activation signal 502. Because intrinsic activation signal 502 is substantially within passband 202 of intrinsic activation sensing circuit 104 and has sufficient relative amplitude to exceed a sensing threshold of intrinsic activation sensing circuit 104, intrinsic activation signal 502 is passed (i.e., detected) by intrinsic activation sensing circuit 104, as indicated at block 504. However, intrinsic activation signal 502 is substantially outside of passband 302 of crosstalk sensing circuit 106. Accordingly, intrinsic activation signal 502 is not passed (i.e., not detected) by crosstalk sensing circuit 106, as indicated at block 506.

Computing device 110 determines whether the signal of interest was detected by crosstalk sensing circuit 106. As such, in the example of FIG. 5, because intrinsic activation signal 502 is detected by intrinsic activation sensing circuit 104, but is not detected by crosstalk sensing circuit 106, computing device 110 correctly identifies intrinsic activation signal 502 as an intrinsic activation signal, as indicated at block 508.

FIG. 6 illustrates a response by CRM device 100 to a crosstalk signal 602. Because crosstalk signal 602 partially overlaps the upper tail of passband 202 of intrinsic activation sensing circuit 104 and has sufficient relative amplitude to exceed a sensing threshold of intrinsic activation sensing circuit 104, crosstalk signal 602 is passed (i.e., detected) by intrinsic activation sensing circuit 104, as indicated at block 504.

Crosstalk signal 602 is also substantially within passband 302 of crosstalk sensing circuit 106 and has sufficient relative amplitude to exceed a sensing threshold of crosstalk sensing circuit 106. Accordingly, crosstalk signal 602 is also passed (i.e., detected) by crosstalk sensing circuit 106, as indicated at block 506. Crosstalk signal 602 is detected substantially concurrently by both intrinsic activation sensing circuit 104 and by crosstalk sensing circuit 106 (e.g., taking into account some timing tolerance to account for different lags between reaching detection thresholds by intrinsic activation sensing circuit 104 and crosstalk sensing circuit 106). Because crosstalk signal 602 is detected by intrinsic activation sensing circuit 104 and crosstalk sensing circuit 106, computing device 110 correctly identifies crosstalk signal 602 as a crosstalk signal (as indicated at block 608), and rejects the false positive detection by intrinsic activation sensing circuit 104 of crosstalk signal 602 as an intrinsic activation signal.

FIG. 7 illustrates a response by CRM device 100 to a crosstalk signal 702. Unlike crosstalk signal 602, crosstalk signal 702 partially overlaps the upper tail of passband 202 of intrinsic activation sensing circuit 104, but does not have sufficient relative amplitude to exceed a sensing threshold of intrinsic activation sensing circuit 104. Accordingly crosstalk signal 702 is rejected (i.e., not detected) by intrinsic activation sensing circuit 104, as indicated at block 504.

Crosstalk signal 702 is also substantially within passband 302 of crosstalk sensing circuit 106 and has sufficient relative amplitude to exceed a sensing threshold of crosstalk sensing circuit 106. Accordingly, crosstalk signal 702 is also passed (i.e., detected) by crosstalk sensing circuit 106, as indicated at block 506. Because crosstalk signal 702 is not detected by intrinsic activation sensing circuit 104 but is detected by crosstalk sensing circuit 106, computing device 110 correctly identifies crosstalk signal 702 as a crosstalk signal, as indicated at block 708.

Figure 8:
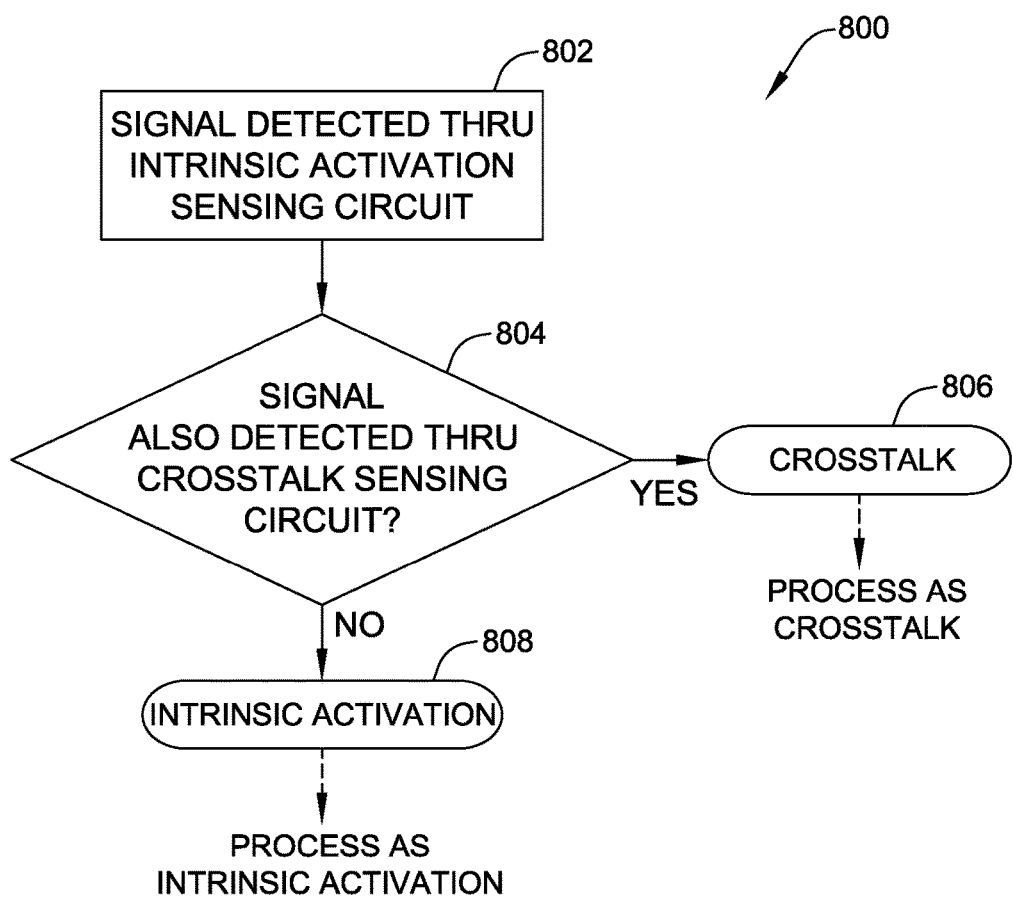
FIG. 8 is a flow diagram of one embodiment of a method for classifying signals.

FIG. 8 is a flow diagram of one embodiment of a method 800 for classifying signals that may be performed, for example, using CRM device 100 (shown in FIG. 1). At block 802, a signal of interest is detected by intrinsic activation sensing circuit 104. At block 804, computing device 110 determines whether the signal of interest was also detected substantially concurrently by crosstalk sensing circuit 106. If the signal of interest was detected by crosstalk sensing circuit 106, it is identified as a crosstalk signal at block 806 and processed accordingly (e.g., ignoring the signal, initiating a crosstalk signal processing algorithm, etc.). Alternatively, if the signal of interest was not detected by crosstalk sensing circuit 106, it is identified as an intrinsic activation signal at block 808 and processed accordingly.

Based on the classification of a signal, appropriate action may be taken (e.g., by a physician, or by an algorithm operating on the CRM device). For example, pacing of a patient's heart may be adjusted based on whether the signal is classified as a crosstalk signal or an intrinsic activation signal. Alternatively, any other suitable actions may be taken in response to the classification.

The systems and methods described herein facilitate accurately classifying signals of interest in a CRM device as either intrinsic activation signals or crosstalk signals. The signals are discriminated by using both an intrinsic activation sensing circuit and a crosstalk sensing circuit. By accurately classifying signals, appropriate action may be taken to address the signals, improving patient care.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A cardiac rhythm management (CRM) device comprising:
   an intrinsic activation sensing circuit configured to pass signals falling within a first passband;
   a crosstalk sensing circuit configured to pass signals falling within a second passband, wherein the second passband contains higher frequencies than the first passband; and
   a computing device communicatively coupled to the intrinsic activation sensing circuit and the crosstalk sensing circuit, the computing device configured to classify a signal of interest as one of an intrinsic activation signal and a crosstalk signal based on whether the signal of interest is passed by the intrinsic activation sensing circuit and the crosstalk sensing circuit, wherein to classify a signal of interest, the computing device is configured to classify the signal of interest as an intrinsic activation signal when the signal of interest is passed by the intrinsic activation sensing circuit and not passed by the crosstalk sensing circuit.

2. The CRM device of claim 1, wherein the second passband has a lower cutoff frequency greater than or equal to 500 Hz.

3. The CRM device of claim 1, wherein the second passband has a lower cutoff frequency greater than or equal to 1000 Hz.

4. The CRM device of claim 1, wherein the second passband has a center frequency equal to approximately 25,000 Hz.

5. The CRM device of claim 1, wherein the CRM device is configured to adjust pacing of a patient's heart based on the classification of the signal of interest.

6. A cardiac rhythm management (CRM) device comprising:
   an intrinsic activation sensing circuit configured to pass signals falling within a first passband;
   a crosstalk sensing circuit configured to pass signals falling within a second passband, wherein the second passband contains higher frequencies than the first passband; and
   a computing device communicatively coupled to the intrinsic activation sensing circuit and the crosstalk sensing circuit, the computing device configured to classify a signal of interest as one of an intrinsic activation signal and a crosstalk signal based on whether the signal of interest is passed by the intrinsic activation sensing circuit and the crosstalk sensing circuit, wherein to classify a signal of interest, the computing device is configured to classify the signal of interest as a crosstalk signal when the signal of interest is passed by the intrinsic activation sensing circuit and passed by the crosstalk sensing circuit.

7. The CRM device of claim 6, wherein the CRM device is configured to adjust pacing of a patient's heart based on the classification of the signal of interest.

8. A cardiac rhythm management (CRM) device comprising:
   an intrinsic activation sensing circuit configured to pass signals falling within a first passband;
   a crosstalk sensing circuit configured to pass signals falling within a second passband, wherein the second passband contains higher frequencies than the first passband; and
   a computing device communicatively coupled to the intrinsic activation sensing circuit and the crosstalk sensing circuit, the computing device configured to classify a signal of interest as one of an intrinsic activation signal and a crosstalk signal based on whether the signal of interest is passed by the intrinsic activation sensing circuit and the crosstalk sensing circuit, wherein to classify a signal of interest, the computing device is configured to classify the signal of interest as a crosstalk signal when the signal of interest is not passed by the intrinsic activation sensing circuit and passed by the crosstalk sensing circuit.

9. A cardiac rhythm management (CRM) device comprising:
   an intrinsic activation sensing circuit configured to pass signals falling within a first passband;
   a crosstalk sensing circuit configured to pass signals falling within a second passband, wherein the second passband contains higher frequencies than the first passband; and
   a computing device communicatively coupled to the intrinsic activation sensing circuit and the crosstalk sensing circuit, the computing device configured to classify a signal of interest as one of an intrinsic activation signal and a crosstalk signal based on whether the signal of interest is passed by the intrinsic activation sensing circuit and the crosstalk sensing circuit, further comprising a pair of sensing electrodes communicatively coupled to the intrinsic activation sensing circuit and the crosstalk sensing circuit.

10. The CRM device of claim 9, wherein the CRM device is configured to adjust pacing of a patient's heart based on the classification of the signal of interest.

11. A method of classifying a signal of interest using a cardiac rhythm management (CRM) device, the method comprising:
    receiving the signal of interest at an intrinsic activation sensing circuit configured to pass signals falling within a first passband;
    receiving the signal of interest at a crosstalk sensing circuit configured to pass signals falling within a second passband, wherein the second passband contains higher frequencies than the first passband;
    determining, using a computing device, whether the signal of interest is passed by the intrinsic activation sensing circuit and the crosstalk sensing circuit; and
    classifying the signal of interest as one of an intrinsic activation signal and a crosstalk signal based on the determination, wherein classifying the signal of interest comprises classifying the signal of interest as an intrinsic activation signal when the signal of interest is passed by the intrinsic activation sensing circuit and not passed by the crosstalk sensing circuit.

12. The method of claim 11, wherein classifying the signal of interest comprises classifying the signal of interest as a crosstalk signal when the signal of interest is passed by the intrinsic activation sensing circuit and passed by the crosstalk sensing circuit.

13. The method of claim 11, wherein classifying the signal of interest comprises classifying the signal of interest as a crosstalk signal when the signal of interest is not passed by the intrinsic activation sensing circuit and passed by the crosstalk sensing circuit.

14. The method of claim 11, wherein receiving the signal of interest at a crosstalk sensing circuit comprises receiving the signal of interest at a crosstalk sensing circuit in which the second passband has a lower cutoff frequency greater than or equal to 500 Hz.

15. The method of claim 11, further comprising pacing a patient's heart based on the classification of the signal of interest.

16. The method of claim 11, wherein receiving the signal of interest at a crosstalk sensing circuit comprises receiving the signal of interest at a crosstalk sensing circuit in which the second passband has a center frequency equal to approximately 25,000 Hz.

17. A computing device for use in classifying a signal of interest detected by a cardiac rhythm management (CRM) device, the computing device comprising:
   a memory device; and
   a processor communicatively coupled to the memory device, the processor configured to:
      determine whether the signal of interest is passed by an intrinsic activation sensing circuit configured to pass signals falling within a first passband;
      determine whether the signal of interest is passed by a crosstalk sensing circuit configured to pass signals falling within a second passband, wherein the second passband contains higher frequencies than the first passband; and
      classify the signal of interest as one of an intrinsic activation signal and a crosstalk signal based on whether the signal of interest is passed by the intrinsic activation sensing circuit and the crosstalk sensing circuit, wherein to classify the signal of interest, the processor is configured to classify the signal of interest as an intrinsic activation signal when the signal of interest is passed by the intrinsic activation sensing circuit and not passed by the crosstalk sensing circuit.

18. The computing device of claim 17, wherein to classify the signal of interest, the processor is configured to classify the signal of interest as a crosstalk signal when the signal of interest is passed by the intrinsic activation sensing circuit and passed by the crosstalk sensing circuit.

19. The computing device of claim 17, wherein to classify the signal of interest, the processor is configured to classify the signal of interest as a crosstalk signal when the signal of interest is not passed by the intrinsic activation sensing circuit and passed by the crosstalk sensing circuit.

20. The computing device of claim 17, wherein to determine whether the signal of interest is passed by a crosstalk sensing circuit, the processor is configured to determine whether the signal of interest is passed by a crosstalk sensing circuit in which the second passband has a lower cutoff frequency greater than or equal to 500 Hz.

* * * * *